United States Patent
Galen et al.

(10) Patent No.: US 7,010,342 B2
(45) Date of Patent: Mar. 7, 2006

(54) METHOD AND APPARATUS FOR DETECTING AND TRANSMITTING ELECTRICAL AND RELATED AUDIO SIGNALS FROM A SINGLE, COMMON ANATOMICAL SITE

(75) Inventors: Peter M. Galen, Portland, OR (US); David B. Swedlow, Danville, CA (US); Steven A. Mahoney, McMinnville, OR (US); Martin Baumer, Carlton, OR (US)

(73) Assignee: Inovise Medical, Inc., Portland, OR (US)

(*) Notice: Subject to any disclaimer, the term of this patent is extended or adjusted under 35 U.S.C. 154(b) by 467 days.

(21) Appl. No.: 10/389,402

(22) Filed: Mar. 14, 2003

(65) Prior Publication Data

US 2003/0176800 A1    Sep. 18, 2003

Related U.S. Application Data

(60) Provisional application No. 60/364,768, filed on Mar. 14, 2002.

(51) Int. Cl.
*A61B 5/04*    (2006.01)

(52) U.S. Cl. ............... 600/513; 600/372; 600/514; 600/528

(58) Field of Classification Search ............... 600/372, 600/403, 421, 513, 514, 528
See application file for complete search history.

(56) References Cited

U.S. PATENT DOCUMENTS

| | | | | |
|---|---|---|---|---|
| 3,455,293 A | * | 7/1969 | Bethune | 600/513 |
| 3,623,479 A | * | 11/1971 | Day | 600/372 |
| 4,362,164 A | * | 12/1982 | Little et al. | 600/382 |
| 4,576,179 A | | 3/1986 | Manus et al. | |
| 4,777,961 A | * | 10/1988 | Saltzman | 600/528 |
| 5,086,776 A | | 2/1992 | Fowler, Jr. et al. | |
| 5,334,990 A | * | 8/1994 | Robinson | 343/840 |
| 5,685,317 A | | 11/1997 | Sjöström | |
| 5,727,549 A | | 3/1998 | Suda et al. | |
| 5,813,404 A | | 9/1998 | Devlin et al. | |
| 6,050,950 A | | 4/2000 | Mohler | |

FOREIGN PATENT DOCUMENTS

WO    WO 88/05282    7/1988

* cited by examiner

Primary Examiner—Robert E. Pezzuto
Assistant Examiner—Brian T. Gedeon
(74) Attorney, Agent, or Firm—Jon M. Dickinson, PC; Robert D. Varitz, PC

(57) ABSTRACT

A sensor designed to collect and convey single-site-related, body-produced electrical and acoustic signals, such as those related to heart activity, where electrical electrode and audio transducer structures lie along a common axis. A portion of the electrical electrode structure forms an acoustic isolating shroud around the audio transducer.

5 Claims, 1 Drawing Sheet

METHOD AND APPARATUS FOR DETECTING AND TRANSMITTING ELECTRICAL AND RELATED AUDIO SIGNALS FROM A SINGLE, COMMON ANATOMICAL SITE

CROSS REFERENCE TO RELATED APPLICATION

This application claims priority to the filing date of U.S. Provisional Patent Application Ser. No. 60/364,768, filed Mar. 14, 2002 for "Reusable ECG/Sound Sensor". The entire contents of that provisional application are hereby incorporated in this application by reference.

INTRODUCTION

The present invention relates to body-activity monitoring, and very specifically to a method and apparatus utilizing a remote, and preferably reuseable and/or discardable, combined electrical and audio sensor which can be applied directly to a person's anatomy to pick up simultaneously an electrical signal, as well as a site-related audio signal, for coupling to external monitoring apparatus. A preferred embodiment of the invention is described in the setting of heart monitoring. It is described in conjunction with a small and largely self-contained sensor unit, wherein an audio transducer, such as a small microphone, is combined along a common detection axis with an acoustic and shrouding structure having an opening, like a circular mouth, which is defined, at least in part, by an annular electrical conductor which functions as an electrically conductive element for picking up an ECG electrical signal. Focus in describing this invention herein in the setting of heart monitoring illustrates the capability of the invention to deal effectively with other types of body-activity electrical and audio signals. Accordingly, the reader should think in parallel about other specific applications in which the invention offers utility.

By combining coaxial and cooperative acoustic and ECG detector/transducers in such a manner, useful common-site heart-related activity, displayed via acoustic signals and time-related ECG electrical signals, can be very usefully delivered to medical personnel for evaluation. While reuseability of the device of this invention, at least for a certain number of successive procedures, is desirable, single-use discardability is also a viable option. The construction of the invention is such that it lends itself to relatively low cost implementation.

With a shrouding structure, at least a part of which functions as an electrical signal pick-up structure, disposed electrically symmetrically with respect to what is referred to herein as a detection axis, and with this structure functioning as an acoustic shroud for a coaxially positioned microphonic pick-up, it is a quite simple matter for someone using the invention quickly and easily to place the device appropriately over a selected anatomical site, with substantial assurance that electrical and acoustic signals derived centrally from that site along the mentioned axis will be quite precisely coordinated positionally relative to one another. This common-site "tight" positioning between acoustic and electrical detectors leads to substantial accuracy in relating heart-produced audio signals with time-synchronous ECG electrical signals presented at the same site where the audio signals are detected.

Various features and important advantages that are offered by the invention will now become more fully apparent as the description which follows is read in conjunction with the accompanying drawings.

DETAILED DESCRIPTION OF THE INVENTION

Figure 1:
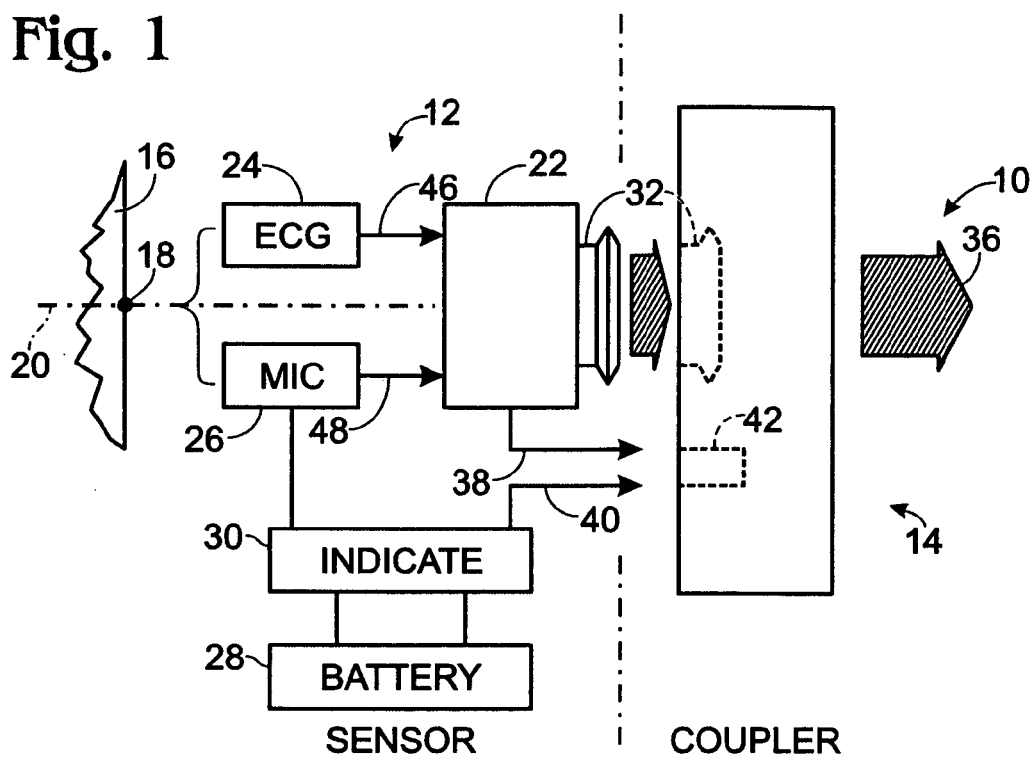
FIG. 1 is a simplified block/schematic view illustrating both the method and the apparatus contemplated by the present invention for detecting and transmitting ECG (or other electrical) and related audio signals from a single, common anatomical site.
Figure 2:
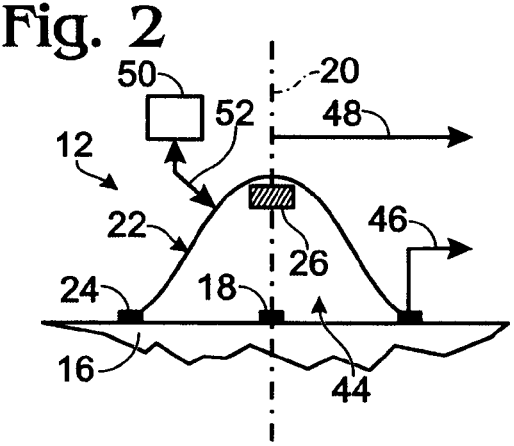
FIG. 2 is a very simplified, stylized cross-sectional view through a sensor unit which defines a detection axis along which appropriate acoustic and electrical elements are symmetrically aligned for common-site reception of related heart-produced signals emanating, effectively, from one selected site on a person's anatomy.
Figure 3:
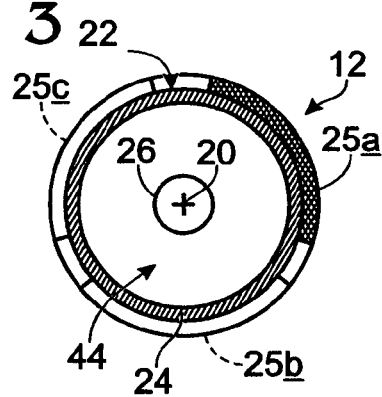
FIG. 3 is a simplified view taken generally from the bottom side of FIG. 2 illustrating coaxial alignment between electrical and acoustic detector elements, and along with FIG. 2, illustrating how the mechanical structure which holds electrical pick-up conductive componentry forms an acoustic sound-gathering and enclosing shroud for the companion acoustic microphone pick-up device employed in the sensor structure.

Turning now to the drawings, and referring first of all to FIGS. 1–3, inclusive, indicated generally at 10 in FIG. 1 are a sensor structure 12 and a coupler structure 14 which are employed in accordance with the present invention for detection and transmission by the sensor structure of what is referred to herein as common-anatomical-site heart-related ECG (or other body-produced electrical) and audio signals that are collected from adjacent a person's anatomy 16, and with reference to a selected site 18 on the surface of that anatomy. The structure of sensor 12 is such that it defines what is referred herein as an event detection axis 20, which, with the sensor structure in place relative to the anatomy as pictured in the figures, is positioned so that the axis passes ideally directly though site 18, as illustrated generally in FIGS. 1 and 2.

Included in sensor structure 12 are a sensor body structure 22, an electrical-signal electrode structure 24, and an audio-signal transducer in the form of a small microphone 26. Also included in the embodiment of sensor structure 12 as pictured herein are a battery 28 and an indicator 30 which is optionally provided to give an indication, when sensor 12 is placed in use, about the charge level of battery 28. This indicator is useful, of course, when the sensor is placed in use, to confirm that appropriate battery power, typically required for biasing operation of microphone 26, is in good supply to do that.

In the particular embodiment of the invention now being described, sensor structure 12 is intended to be removably couplable to a coupler unit, such as the one previously mentioned and illustrated at 14 in FIG. 1, through a snap-together connect/disconnect structure shown generally at 32 in FIG. 1. With all of the elements pictured in the figures connected appropriately for operation, and with sensor 12 and coupler 14 so interconnected as just briefly mentioned, signal flow takes place between the sensor and the coupler as illustrated by the broad shaded arrow 34 in FIG.1, with such signal information passing through the coupler, as indicated by broad shaded arrow 36 in FIG. 1, outwardly therefrom toward external monitoring structure (not illustrated) which is employed to receive and enable review and analysis of signal information thus provided. As an operating convenience, two conductive connections which are shown generally by arrow-headed lines 38, 40 in FIG. 1 become conductively connected through a conductive path shown by dashed lines at 42 in FIG. 1 within coupler 14 to establish a battery powering connection for microphone 26.

It will clear from a look at FIG. 1 that electrode structure 24 and transducer or microphone 26 are not there pictured as lying along common detection axis 20. This, of course, is because FIG. 1 is intended to provide a block/schematic diagram generally of componentry and how such componentry is interconnected for cooperation in sensor 12. However, in FIGS. 2, 3 and 4, one can clearly see an important feature of the present invention which is, namely, that electrode structure 24 and microphone 26 are indeed essentially symmetrically aligned at spaced locations distributed on and along detection axis 20. Preferably, electrode structure 24 takes the form of a continuous annular ring, seen especially well in FIG. 3, which circumsurrounds axis 20, with this axis centered on the center of curvature of this ring. Such a ring is said to possess electrical symmetry with respect to axis 20, and this is an important consideration with respect to the way in which electrical signals, such as ECG signals, that are derived through structure 24 can be treated as emanating essentially from selected anatomical site 18 which is preferably intersected by axis 20 with sensor 12 in use.

Further, and according a feature of the invention, electrode structure 24 forms part of, or is appropriately joined to, the sensor body structure 22 in such a fashion that it effectively defines the perimeter of the open side of an enshrouding volume of space, which is a body of revolution, 44 within sensor structure 12. In FIG. 2, volume 44 is shown in a fairly simplistic manner as having a somewhat bell-shaped cross section, with microphone 26 residing effectively acoustically within this volume along axis 20, and spaced from electrode 24 as shown. Illustrated at 46, 48 in FIG. 1 and FIG. 2 are lines which represent electrical conductive paths that communicate signals directly from electrode structure 24 and transducer 26, respectively.

Preferably, when sensor structure 12 is placed on the anatomy for use with respect to collecting information effectively from site 18, the contacting surface of structure 24 carries a conventional, electrically conductive, adhesive attaching gel which forms a good electrical connection with the anatomy, and which, additionally, seals volume of space 44 against inside/outside air flow. By doing this, the volume of space which is designated 44 effectively operates to focus and isolate for reception by acoustic transducer 26 just those audio sounds which are site-related, and which, in the illustration now being given, emanate apparently from anatomy site 18. Sealing of space 44 by contacting of the anatomy with conductor 24, and doing so in a manner whereby an enshrouding acoustic volume, such as volume 44, results, plays an important role in effectively isolating for attention by transducer 26 the very heart-produced audio signals which are directly related with ECG electrical signals that are picked up from and through electrode structure 24 in the specific application now being described. With electrode structure 24 being positioned in an electrically symmetric fashion with respect to site 18, picked-up electrical signals can be viewed as if they were emanating directly and only from site 18.

In terms of sealing the volume of space designated 44, a modified form of the invention may include an appropriate pump and fluid-coupling system, such as that represented schematically by a block 46 and a double-arrow-headed line 52 in FIG. 2. Any suitable construction for this can be employed. Pumping can reduce, to below atmospheric, the pressure within volume 44 with the sensor in place on the anatomy, and such behavior helps to lock the sensor in place, and to improve signal-to-noise ratio with respect to the microphone.

Figure 4:
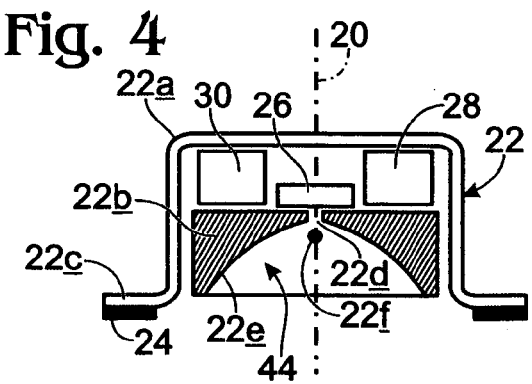
FIG. 4 is a simplified cross-sectional view taken generally from the same point of view employed in FIG. 3, illustrating one kind of interrelated mechanical componentry which may be used to construct a sensor device in accordance with the present invention.

In FIG. 4, the very simplified general schematic layout pictured in FIG. 2 is more definitively illustrated in a form, though certainly not the only form, in which one might choose to construct the various components for and within sensor 12. Components, and their respective, relative locations, are not drawn necessarily to scale, or with mechanical precision, in this drawing Given that, here one can see that the sensor body structure includes an outer shell 22a, and an inner insert 22b which fits snuggly and coaxially within shell 22a. Shell 22a includes an outwardly radially-extending flared skirt 22c, the underside of which carries electrode structure 24.

Insert 22b is shaped to define previously mentioned spatial volume 44 as shown, and where axis 20 meets insert 22b, the insert is provided with an axial through-bore which is shown at 22d. Whereas in FIG. 2 spatial volume 44 is shown defined by a curvilinear, generally bell-shaped outline, in FIG. 4 this volume is shown to be defined within insert 22b by a generally parabolically curved surface 22e. Other kinds of surface curvatures, such as a spherical curvature, may, of course, be used. In the particular structure pictured in FIG. 4, through-bore 22d opens to volume 44 close to, but somewhat spaced from and "behind" (above in FIG.4) the focal point 22f of surface 22e, and microphone 26 is seen to be positioned just above this through-bore in FIG. 4

Battery 28 and indicator structure 30 are shown as simple block forms in FIG. 4, occupying space above insert 22b, and between this insert and the upper portion of body structure shell 22.

It should be understood that while a more specific arrangement of components is pictured for sensor 12 in FIG. 4, there are many different kinds of arrangements which offer the features of the present invention that do not necessarily require the organization pictured in FIG. 4.

As was mentioned earlier, one feature of the invention is that conductive electrode structure 24 is designed to be electrically symmetric with respect to and centered upon detection axis 20. This is illustrated in the preferred embodiment of the invention as being accomplished by incorporating a conductive electrode structure 24 which is a continuous annular ring-like structure, as is shown in light shaded outline in FIG. 3. Other forms of symmetrically distributed electrode structure can of course be employed, and one such other possibility is generally illustrated in FIG. 3 as including three, arcuately distributed, equiangular segments 25a, 25b, 25c that are distributed symmetrically about axis 20. Segment 25a is darkly shadowed in FIG. 3 so that it will clearly stand out in view, whereas segments 25b, 25c are show only in dashed lines in this figure.

The special features of the apparatus of this invention have thus now been described, and recognition of the variability in implementation of these features has been noted.

The unique methodology offered by the invention can be expressed as being a method for detecting and transmitting common-anatomical-site, body-related electrical (such as ECG) and audio signals collected from adjacent a person's anatomy, and including the steps of: (a) establishing a signal-detection axis; (b) positioning an audio-signal transducer on that axis to collect audio signals progressing in one direction generally along the axis toward one side of that transducer; (c) providing electrical-signal electrode structure disposed electrically centrally relative to the established signal-detection axis, and located toward, and spaced from, the mentioned one side of the audio signal traducer; and (d) collectively positioning the axis, the transducer and the electrode structure relative to a selected surface site in a person's anatomy, whereby the axis passes through that site, the electrode structure lies in conductive contact with the anatomy in a manner which is generally symmetrical relative to the site, and the audio transducer is spaced from the site. In a more particular sense, that same broadly defined method can be further defined as one wherein the step of providing electrical-signal electrode structure includes mechanically and acoustically shrouding the transducer in a defined volume of space which has a perimetered open side, and positioning axially symmetrically arranged electrical conductor structure in a manner which is distributed appropriately along the perimeter of the mentioned open side of the enshrouding volume of space.

Yet another way of describing the methodology of this invention is to characterize it as a method for detecting and transmitting common-anatomical-site, body-related electrical and audio signals that are collected from adjacent a person's anatomy, including the steps of: (a) symmetrically aligning acoustic and electrically-conductive sensor components along a common event detection axis; and (b) then utilizing such aligned components relative to a single common anatomical site to detect respectively related audio and electrical signals that effectively emanate from that site generally along the common event detection axis.

Accordingly, while a preferred and best mode embodiment of the invention, several variations thereof, and a preferred and best mode manner of practicing the invention, have been described and illustrated herein, it is appreciated that variations and modifications may be made within the scope of the invention.

We claim:

1. Apparatus for detecting and transmitting single, common-anatomical-site, single, body-related ECG electrical and audio signals collected from adjacent a person's anatomy comprising sensor body structure defining a common-anatomical-site detection axis, electrical-signal electrode structure carried on said sensor body structure, and disposed in spaced electrically, symmetrically centered relationship with regard to said axis, contactable, during use of the apparatus, with a person's anatomy in a manner generally arrayed around the selected anatomical site, and structured to collect effectively a single ECG electrical signal, and audio-signal transducer structure also carried on said body structure and disposed directly on said axis, organized to detect body-related audio signals delivered to it from the selected, single site.

2. The apparatus of claim 1, wherein said sensor body structure includes an open-sided volume of revolution centered substantially on said axis, and possessing a perimeter that substantially defines said volume's said open side, said electrode structure is positioned generally at said perimeter, and said transducer structure is exposed directly to said volume.

3. The apparatus of claim 2, wherein said electrode structure includes at least one annular continuum conductor substantially centered on said axis.

4. The apparatus of claim 3, wherein said volume is at least partially defined by concavely curved surface structure, and said transducer lies immediately adjacent said surface structure.

5. A method for detecting and transmitting single, common-anatomical-site body-related ECG electrical and audio signals collected from adjacent a person's anatomy comprising establishing a signal-detection axis, positioning an audio-signal transducer directly on such axis to collect audio signals progressing in one direction generally along the axis toward one side of the transducer, providing ECG electrical-signal electrode structure disposed electrically centrally relative to the established axis, spaced from the mentioned one side of the transducer, and structured to collect effectively a single ECG electrical signal, and collectively positioning the axis, the transducer, and the electrode structure relative to a selected surface site in a person's anatomy, whereby the axis passes through that site, the electrode structure lies in conductive contact with the anatomy in a manner which is generally symmetrical relative to the site, and the transducer is spaced from the site.

* * * * *